(12) United States Patent  (10) Patent No.: US 7,917,228 B2
Wenger  (45) Date of Patent: Mar. 29, 2011

(54) MEDICAL LEAD ADAPTOR ASSEMBLY

(75) Inventor: William K. Wenger, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 338 days.

(21) Appl. No.: 10/436,770

(22) Filed: May 13, 2003

(65) Prior Publication Data
US 2004/0230267 A1  Nov. 18, 2004

(51) Int. Cl.
A61N 1/00 (2006.01)
(52) U.S. Cl. ...................................................... 607/116
(58) Field of Classification Search .................... 607/37, 607/115, 116, 119; 128/784, 786; 29/858; 248/371; 439/909
See application file for complete search history.

(56) References Cited

U.S. PATENT DOCUMENTS

| | | | | |
|---|---|---|---|---|
| 4,278,316 A | * | 7/1981 | White | 439/831 |
| 4,944,088 A | | 7/1990 | Doan et al. | 29/858 |
| 4,951,687 A | | 8/1990 | Ufford et al. | 128/786 |
| 5,007,435 A | | 4/1991 | Doan et al. | 128/784 |
| 5,241,957 A | | 9/1993 | Camps et al. | 607/119 |
| 5,354,326 A | | 10/1994 | Cross et al. | |
| 5,560,358 A | * | 10/1996 | Arnold et al. | 600/373 |
| 5,740,261 A | * | 4/1998 | Loeppert et al. | 381/355 |
| 5,782,892 A | | 7/1998 | Castle et al. | 607/37 |
| 5,931,861 A | * | 8/1999 | Werner et al. | 607/115 |
| 6,024,702 A | * | 2/2000 | Iversen | 600/378 |
| 6,343,233 B1 | | 1/2002 | Gravlin et al. | |
| 6,536,286 B1 | * | 3/2003 | Moyer et al. | 73/716 |
| 6,788,259 B2 | * | 9/2004 | Amano et al. | 343/702 |
| 6,805,665 B1 | * | 10/2004 | Tatsuno et al. | 600/112 |
| 6,854,994 B2 | * | 2/2005 | Stein et al. | 439/218 |
| 6,912,423 B2 | * | 6/2005 | Ley et al. | 607/37 |
| 7,130,699 B2 | * | 10/2006 | Huff et al. | 607/116 |
| 7,530,542 B2 | * | 5/2009 | Boyce et al. | 248/371 |
| 2002/0040185 A1 | * | 4/2002 | Atalar et al. | 600/423 |

(Continued)

FOREIGN PATENT DOCUMENTS
DE 199 38 960 2/2001

(Continued)

OTHER PUBLICATIONS

"Cable Connector For Electrical Measurements on Pacing Leads with IS-1 Connectors", Research Disclosure, Kenneth Mason Publications, Hampshire, GB, No. 395, Mar. 1, 1997, p. 143, Bibliographic data only.

(Continued)

Primary Examiner — George Manuel
(74) Attorney, Agent, or Firm — Carol F. Barry

(57) ABSTRACT

An adaptor, including a housing and a flexible circuit, facilitates electrical connection between a connector of an implantable medical lead and an external medical device. The adaptor housing includes an inner surface forming a longitudinally extending connector receptacle and a first portion of the flexible circuit is adapted to be positioned within the connector receptacle, substantially conforming to the inner surface, such that at least one contact portion of the flexible circuit is directed inward and positioned in a location corresponding with at least one ring contact of the lead connector when the lead connector is engaged within the receptacle. A second portion of the flexible circuit is adapted to reside outside the housing such that at least one contact pad, coupled to the at least one contact portion via a conductive pathway, is accessible for coupling to at least one contact element of the external medical device.

28 Claims, 9 Drawing Sheets

U.S. PATENT DOCUMENTS

2002/0198582 A1* 12/2002 Edell et al. .................... 607/116
2003/0068914 A1* 4/2003 Merry et al. .................. 439/259
2003/0120327 A1* 6/2003 Tobritzhofer et al. ........ 607/116
2004/0147822 A1* 7/2004 Al-Ali et al. .................. 600/323

FOREIGN PATENT DOCUMENTS

WO          03/053516          7/2003

OTHER PUBLICATIONS

P0011376.01 (PCT/US2004/006884) PCT Notification of Transmittal of the International Search Report.
Cable Connector For Electrical Measurements on Pacing Leads with IS-1 Connectors, Research Disclosure, Kenneth Mason Publications, Hampshire, GB, No. 395, Mar. 1, 1997, p. 143.

* cited by examiner

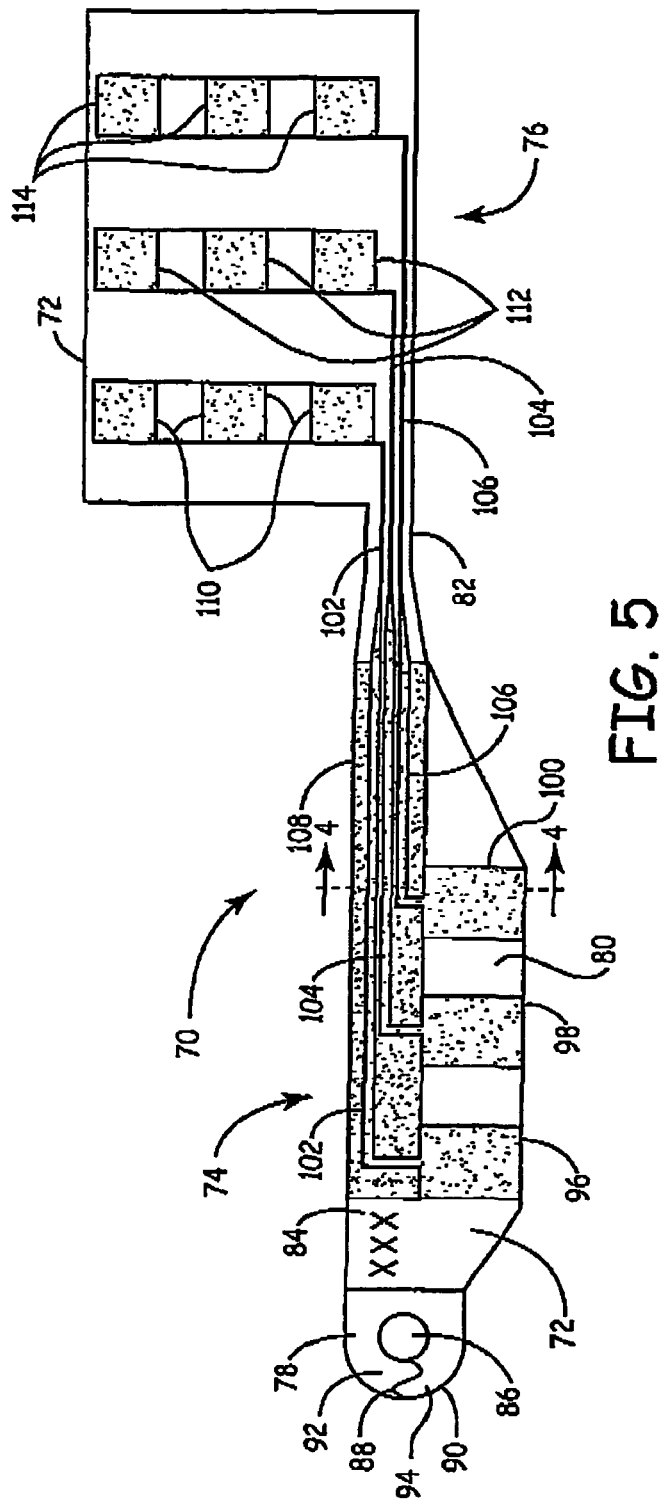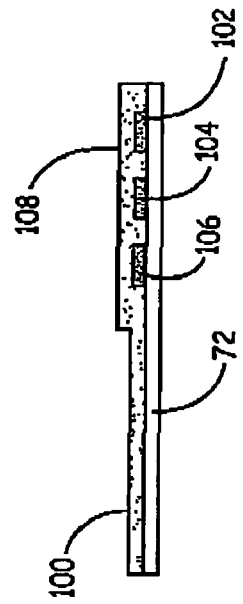

MEDICAL LEAD ADAPTOR ASSEMBLY

CROSS REFERENCE TO RELATED APPLICATION

Cross-reference is hereby made to commonly assigned related U.S. Applications filed concurrently herewith: Ser. No. 10/436,776 to Timothy Holleman et al., entitled "Medical Lead Adaptor Assembly" and Ser. No. 10/436,960 to Frank Skubitz et al., entitled "Medical Lead Adaptor Assembly".

FIELD OF THE INVENTION

The present invention generally relates to a medical lead adaptor assembly, and in particular, the present invention relates to a medical lead adaptor assembly facilitating a temporary connection between a medical lead of an implantable medical device and an external medical device.

BACKGROUND OF THE INVENTION

The earliest instances of relatively prolonged cardiac stimulation, namely cardiac pacing, of a patient's heart was effected through implanted cardiac leads attached to the heart muscle at distal electrode ends and extending through an incision in the patient's skin. To effect unipolar pacing of the heart, a single such implantable pacing lead was employed in conjunction with a subcutaneously implanted or skin-surface attached return electrode coupled to an external lead conductor. To effect bipolar pacing of the heart, two such implantable pacing leads were implanted with the electrode ends implanted a distance apart. The attachment of the proximal ends of the lead conductors to the temporary cardiac pacemaker connector elements was initially effected by simply stripping insulation from the proximal conductor ends, and inserting and securing the bare conductor ends in transverse openings in threaded posts. Later, finished connector pins were formed at the proximal connector ends of the lead bodies that could be inserted into the end openings of thumb nuts and connector posts.

Implantable pacing leads evolved into permanent, unipolar and bipolar, endocardial and epicardial, pacing leads for chronic implantation in a patient. The proximal electrical connector assemblies were then connected with connector elements of a totally implanted, cardiac pacemaker pulse generator. To withstand stress, implantable pacing lead conductors were formed of coiled wire and inserted within an insulative lead body lumen, thereby providing a coiled wire lumen that was sized to receive a stiffening stylet wire to assist tranvenous implantation of the endocardial pacing leads. The proximal end of the coiled wire conductor was attached to a tubular connector pin at the terminus of the lead connector and shaped to be received in the connector assembly of the implantable pacemaker pulse generator. In the case of endocardial permanent pacing leads, the connector or pin was formed with a lumen therein aligned with the coiled wire lumen so that the stiffening stylet wire could be inserted down the length of the lead body during the transvenous introduction and withdrawn after placement of the distal electrode was achieved. Many of these features are employed in current permanent pacing leads.

More recently, bipolar and multi-polar permanently implantable pacing leads and leads for use in pacing and cardioversion/defibrillation (collectively referred to as permanent implantable cardiac leads) have been developed using coaxially arranged, coiled wire conductors and/or parallel-wound, multi-filar coiled wire conductors. In the case of endocardial cardiac leads, the stylet wire lumen is employed to receive the stiffening stylet wire for implantation as described above. The proximal connector end assemblies are formed with at least two spaced apart lead connector elements arranged in-line from a proximal lead connector pin to at least one or more distally located ring-shaped element or lead connector ring. Typical bipolar in-line lead connector assemblies for multi-filar, coiled wire conductors are shown, for example, in commonly assigned U.S. Pat. Nos. 4,944,088 and 4,951,687 and 5,007,435, respectively, the teachings of which are hereby incorporated by reference.

Unipolar and bipolar, temporary endocardial pacing leads and temporary epicardial heart wires were also developed for implantation of the distal electrode(s) thereof in contact with the endocardium or sutured through the epicardium of the hearts of hospitalized patients. The lead body size of these temporary pacing leads and heart wires has typically been smaller than that of permanent cardiac leads because of the absence of an internal wire coil lumen for receiving a stylet wire. Still, in the case of bipolar temporary pacing leads and heart wires, either a lead connector pin and ring set are employed providing a pair of lead connector pins.

During or after implantation of the implantable cardiac lead(s), an external pacing system analyzer (PSA), e.g. MEDTRONIC® Model No.'s 2290 and 8090, is attached to the proximal lead connector end assembly accessible through the incision to assess the performance of the system and verify proper lead placement. It is necessary in some cases to use either a disposable or a reusable "surgical cable" adaptor to complete the connection between the implanted lead and the external pacing system analyzer.

Some patient and surgical cable adaptors constitute a connector assembly at a first end that is compatible with the PSA or temporary pacemaker terminals, a cable including conductors extending from the first end to a second end, and lead connector element connectors at the second end. Typically, two to four conductors are included in the cable, and a set of two or four alligator clips are provided at the second end for attachment to one or more lead connector rings and a pin of one or two implantable cardiac leads.

In the case of a permanent pacing lead having a stylet wire fitted within the lead lumen and projecting out proximally through the connector pin, alligator clips are utilized that attach across the connector rings and pins. However, such an attachment is not as secure and electrically isolated as would be desirable. It is undesirable to either lose the connection or to allow an electrical static discharge or other shock or impulse to reach the heart through the exposed lead connector ends. Furthermore, it has been observed that the careless use of alligator clips can damage the insulation sheathes adjacent to the lead connector end ring or connector pins. This problem is further complicated in the case of leads having a plurality of contact rings separated by insulative sealing surfaces. That is, not only is there a potential for shorting between alligator clips and/or test probes, but such clips may cause damage to the insulation/sealing areas adjacent the contact rings.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and:

FIG. 5 is a plan view of an alternate embodiment of a flexible circuit for use in conjunction with the present invention;

FIG. 6 is a cross-sectional view taken along line 4-4 in FIG. 5;

DETAILED DESCRIPTION OF THE INVENTION

The following detailed description of the invention is merely exemplary in nature and is not intended to limit the scope, applicability, or configuration of the invention in any way. Rather, the following description provides a convenient illustration for implementing exemplary embodiments of the invention. Various changes to the described embodiments may be made in the function and arrangement of the elements described herein without departing from the scope of the invention.

The invention is described in connection with a number of embodiments of medical lead adaptor assemblies, each of which facilitate electrical coupling between the proximal lead connector end assembly of a cardiac or similar lead and an external medical device. The lead adaptor is capable of being coupled to external electrical conductors by means of conductive probes, clips, and the like. The inventive medical lead adaptor assembly may be configured to accept lead connectors that may or may not include a stylet wire or a guide wire passing therethrough. Furthermore, the inventive lead adaptor may be utilized in conjunction with leads having compatible lead connector element dimensions; i.e. compatible spacing between and diameters of ring contacts. Of course, the medical lead adaptor assembly in accordance with the present invention may be provided with different dimensions so as to accommodate a variety of cardiac or other types of leads.

Figure 1A:
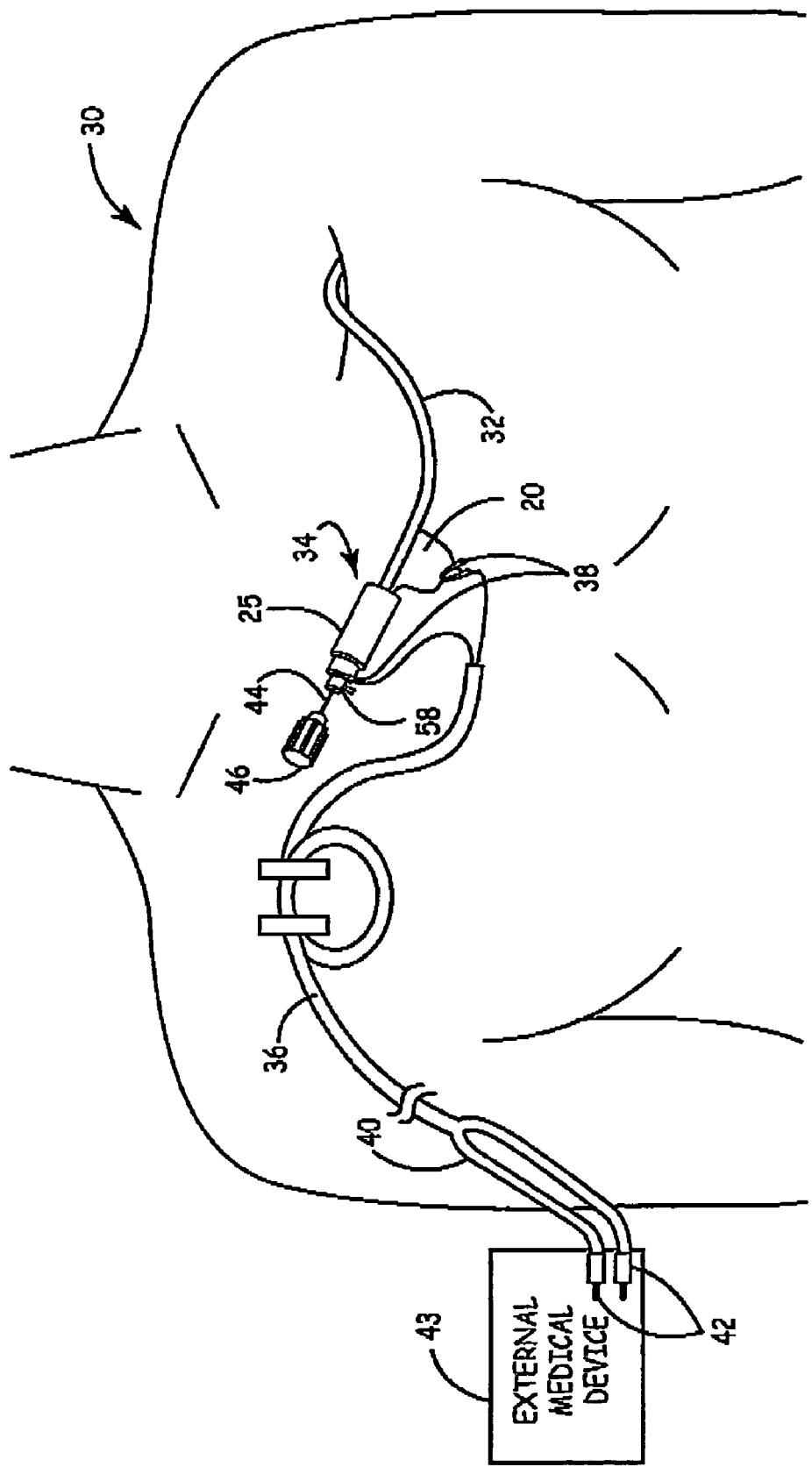
FIG. 1A is a simplified schematic view of a cardiac lead implanted in a patient and coupled to an external medical device by means of the inventive medical lead adaptor assembly.
Figure 2:
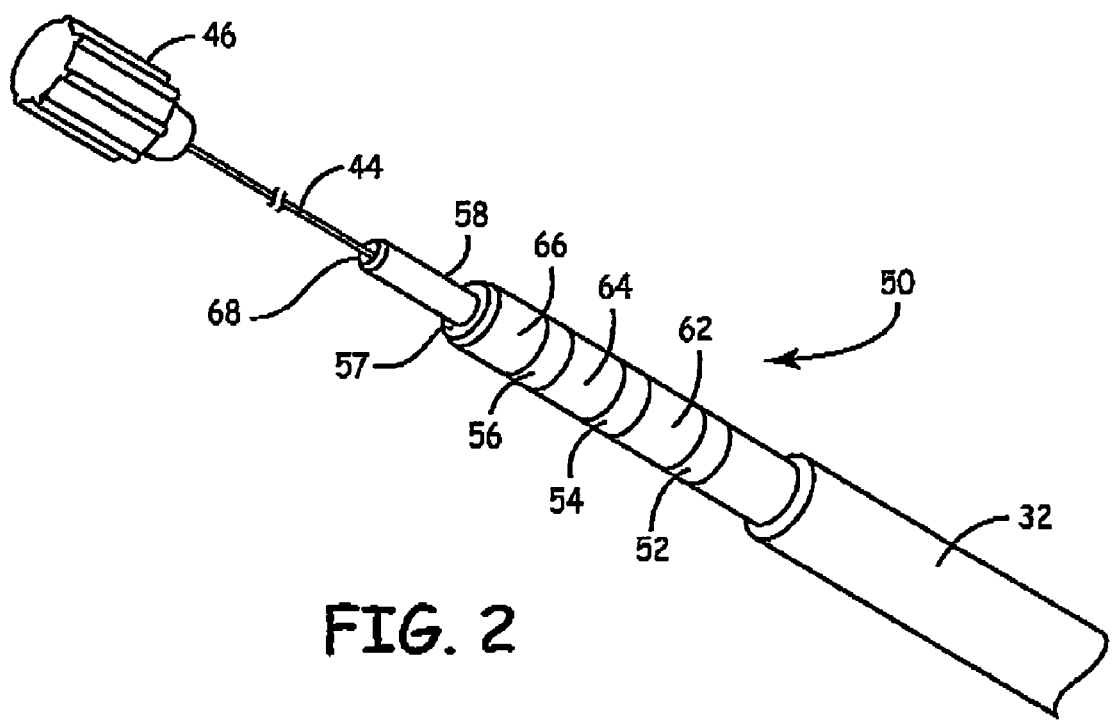
FIG. 2 is an isometric view of a lead connector assembly capable of being received into an inventive medical lead adaptor.

FIG. 1A is a simplified schematic view of a medical lead implanted in a patient and coupled to an external medical device by means of the inventive medical lead adaptor assembly. As can be seen, a proximal portion of an implantable cardiac lead is shown in part and includes an elongated implantable lead body 32 extending from a lead adaptor assembly 34 (to be described in detail herein below) toward the distal cardiac lead end (not shown). The distal cardiac lead end includes at least one electrode implanted in contact with a heart chamber of patient 30. The lead connector (shown in FIG. 2 as 50) is received within adaptor 34 as will be described hereinafter for facilitating rapid electrical connection between lead body 32 and external medical device 43 by means of cable 36 and one or more contact elements, for example alligator clips 38. The proximal end 40 of cable 36 is provided with means for electrical connection to one or more external medical devices by means of, for example, connectors 42 that engage connector terminals associated with the external medical device. The external medical device connection terminals may take any form, such as those associated with the above-referenced MEDTRONIC® Models 2290 and 8090 or Model 5348 and 5388 temporary pacemakers. A stylet wire 44 having a proximal end coupled to stylet knob 46 extends from a lumen in lead connector assembly 50 (FIG. 2). A stylet wire 44 extends through connector assembly 50 and lead body 32; alternately an interventional guide wire may extend through connector assembly 50 and lead body 32. In this manner, stylet wire 44, or a guide wire, may be rotated, axially extended, withdrawn, etc., to aid in implantation of lead body 32.

Figure 1B:
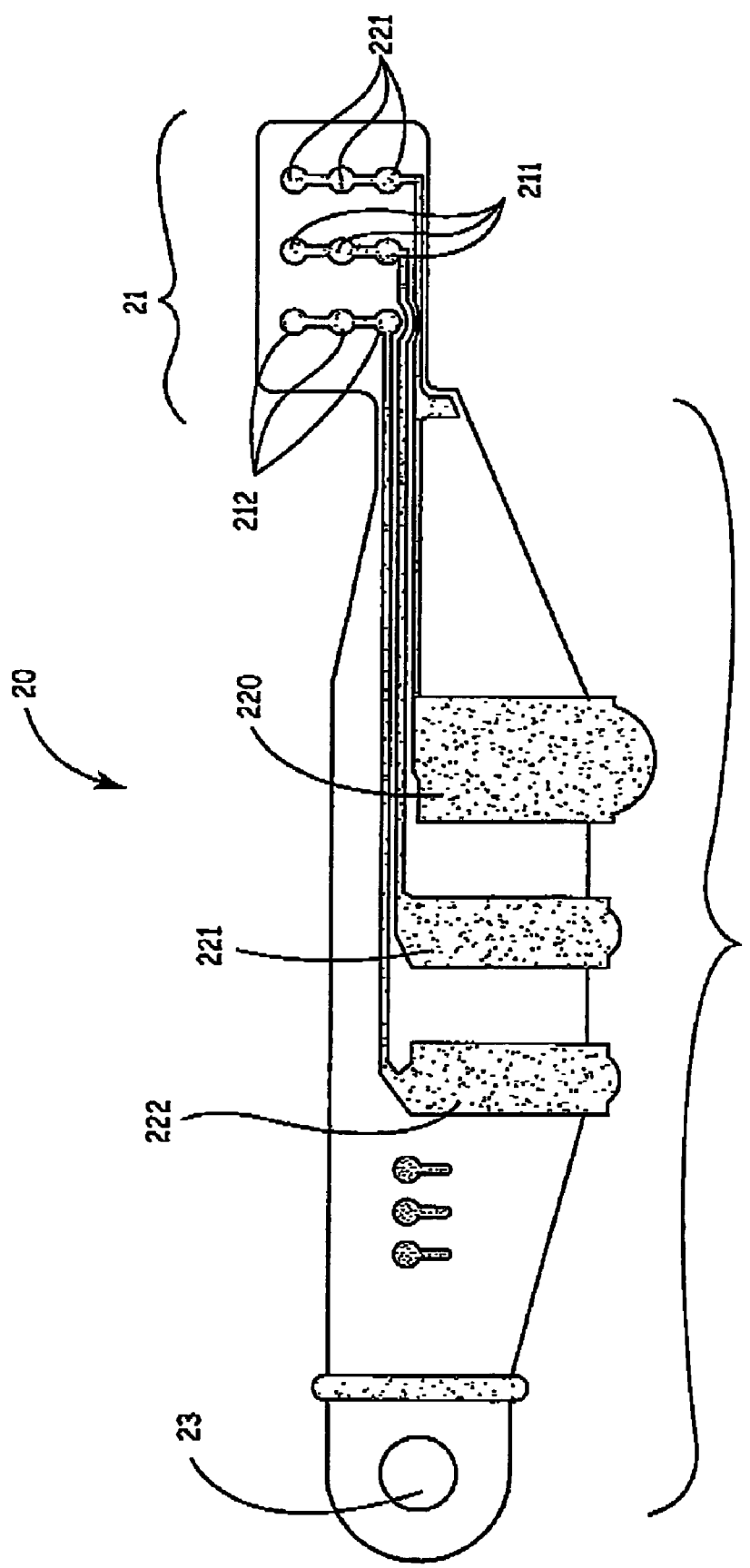
FIG. 1B is a plan view of a flexible circuit for use in conjunction with embodiments of the present invention.

Embodiments of the inventive medical lead adaptor assembly 34 include a flexible circuit 20 and a housing 25; a first portion 21 (FIG. 1B) of flexible circuit 20 is contained within housing 25 and a second portion 22 (FIG. 1B) of flexible circuit 20 extends from housing 25 providing relatively large contact pads 220, 221, and 222 (FIG. 1B) to which alligator clips 38 may be coupled, as illustrated in FIG. 1A. FIG. 1B is a plan view of flexible circuit 20 for use in conjunction with embodiments of the present invention. Flexible circuit 20, formed by a conductive pattern on a flexible substrate, is configured to conform to positions of contacts on connector 50 (FIG. 2) as will be further described herein below. First portion 21 of the flexible circuit 20 is adapted to be rolled or folded and positioned within a housing (e.g. a generally cylindrical tube or receptacle) and includes raised electrical contact portions or protrusions 210, 211, and 212 such as folds or dimples, mechanically or thermally formed, that extend radially inward to mechanically and electrically engage corresponding contacts on connector 50 (e.g. 52, 54 and 56 in FIG. 2) inserted into the housing. Flexible circuit 20 further includes conductive pathways extending from first portion 21 to second portion 22 and coupling contact portions 210, 211, and 212 to corresponding contact pads 220, 221, and 222, which are generally flat and to which alligator clips may be attached. Cutouts may be provided in first portion 21 of flexible circuit 20 to substantially eliminate buckling when the flat substrate is rolled into a tube. A pattern of contact portions on the flexible circuit is sized and dimensioned to match the contact pattern of a corresponding connector. Processes and materials used to make flexible circuit 20 are well known to those skilled in the art of flexible circuit technology.

Second portion 22 may also function as a keeper when the connector is withdrawn from housing 25; according to one embodiment an aperture 23 retains adaptor assembly 34 on lead body 32 (FIG. 2) making it readily accessible should it become necessary to reinsert the connector into the adaptor 34 for additional testing and preventing adapter assembly 34 from migrating beyond the sterile field (e.g. falling to the floor) and/or becoming lost within the folds of sterile drapes that cover the patient.

FIG. 2 is an isometric view of a lead connector assembly capable of being received into an adaptor according to the present invention, various embodiments of which are described herein. Connector 50 at the proximal end of lead body 32 includes contact rings 52, 54 and 56 and a pin contact 58, each electrically coupled to conductors within lead body 32 and electrically isolated from each other by insulative layers within lead body 32 and by sealing rings 62, 64, and 66. Extending from a lumen 68 in lead connector 50 is stylet wire 44 which may be manipulated by means of stylet knob 46 as described above. While connector 50 has been shown as comprising three contact rings and three insulative sealing rings, it should be clear that the inventive medical lead adaptor assembly is equally applicable to connectors having a different number of contact rings including a single contact ring as is typical of IS-1 connectors.

Figure 3:
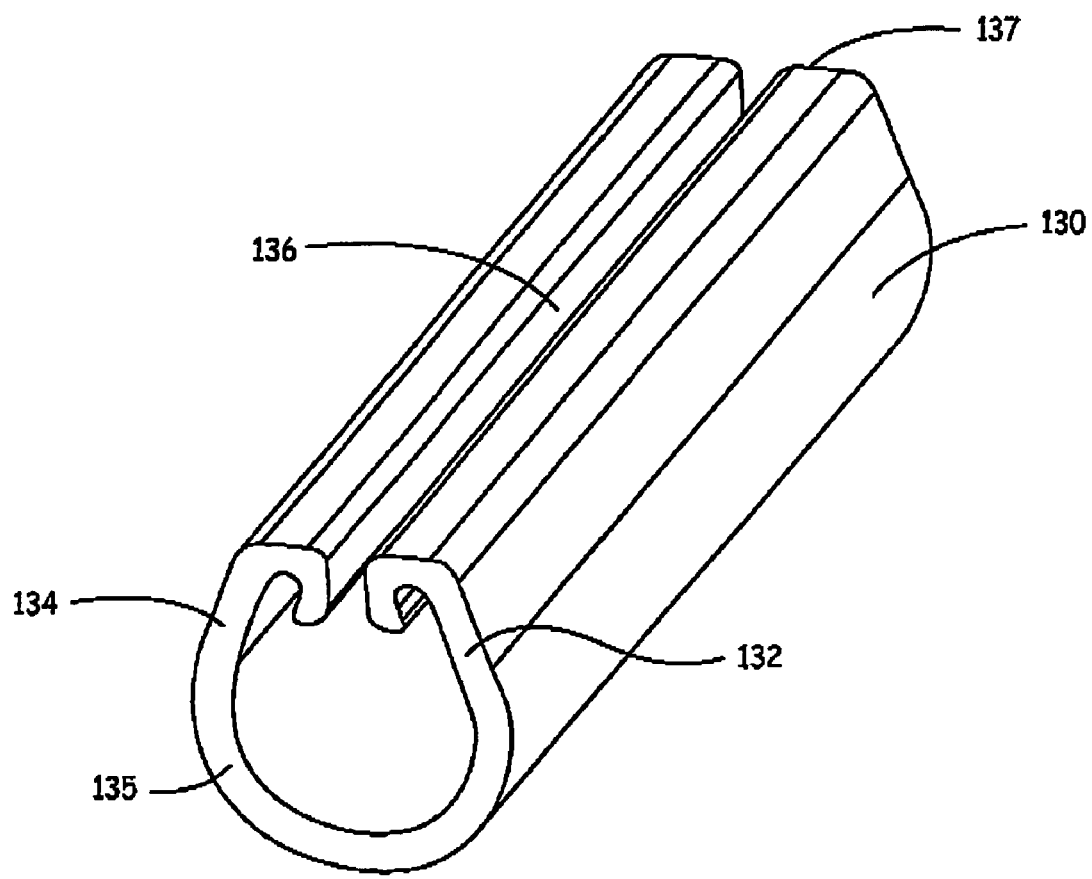
FIG. 3 is an isometric view of a housing for a portion of the flexible substrate shown in FIG. 1B in accordance with one embodiment of the present invention.
Figure 4:
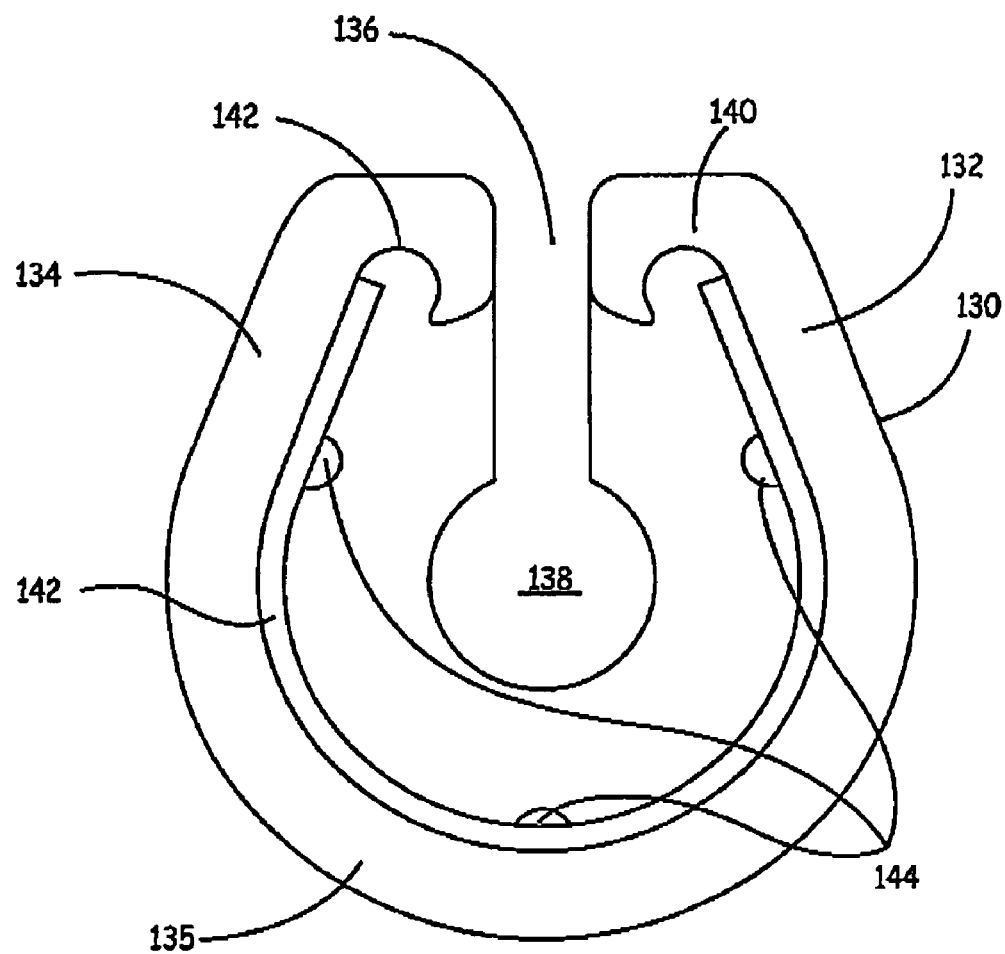
FIG. 4 is an end view of the housing shown in FIG. 3 containing a flexible circuit having electrically conductive dimples thereon.

FIG. 3 and FIG. 4 are isometric and end views respectively of an embodiment of a housing for receiving the rolled or folded contact portion 21 (FIG. 1B) of flexible circuit 20. In this case, the housing is capable of receiving a connector 50 (FIG. 2) of a cardiac lead 30 (FIG. 2). An elongate housing 130 has a generally horseshoe-shaped cross-section defined by leg portions 132 and 134 having a space or channel 136 therebetween dimensioned to receive stylet wire 44. Housing 130 includes an open distal or first end 135 dimensioned to receive connector 50 and a proximal or second end 137 including an opening or aperture 138 dimensioned to allow passage of pin contact 58 while providing a stop for a proximal face 57 of connector 50 (FIG. 2). Referring to FIG. 4, each of leg portions 132 and 134 is provided with a curved capture portion 140 and 142 respectively for securing a flexible circuit 142 having conductive dimples 144 thereon in place within housing 130. Flexible circuit 142 corresponds to first portion 21 shown in FIG. 1B.

FIG. 5 is a plan view of an alternate embodiment of a flexible circuit 70 for use in conjunction with the present invention. Flexible circuit 70 includes a flexible substrate 72 configured to form an external contact portion 74 and an internal contact portion 76. External contact portion 74 comprises a keeper section 78, a first conductor section 80 and an indicia bearing section 84 which may bear indicia identifying a type of lead connector for which an adaptor assembly, into which circuit 70 is integrated, is compatible.

Keeper section 78 comprises an opening 86 therethrough and a slit 88 extending from edge 90 to opening 86 and defining first and seconds flaps 92 and 94. Flaps 92 and 94 may be spread apart so as to permit lead body 32 to be positioned within opening 86 and thus retain an adaptor assembly including circuit 70 within the sterile field. When the testing process is complete, the adaptor assembly may be simply pulled away from lead body 32 causing flaps 92 and 94 to spread thus permitting lead body 32 to exit opening 86.

First conductor section 80 is generally flat and comprises first, second, and third contact pads 96, 98, and 100 respectively electrically coupled to conductive pathways 102, 104, and 106 respectively. As illustrated in FIG. 6, which is a cross-sectional view taken along line 4-4 in FIG. 5, conductive pathways 102, 104, and 106 are protected by an insulative layer 108. Contact pads 96, 98, and 100 are positioned and dimensioned so as to facilitate attachment of, for example, alligator clips 38 (FIG. 1A) and thereby effectuate electrical coupling between the implanted device and the external medical device. Conductive pathways 102, 104, and 106 extend into a connector region 82. While three conductive pathways 102, 104, and 106 are shown in FIG. 5, it should be appreciated that the number of conductive pathways may vary to accommodate any number of connector contacts associated with the lead of the implantable medical device.

Internal contact portion 76 includes three rows of contact areas in the form of conductive protrusions 110, 112, and 114, each row electrically coupled to a conductive pathway 116, 118, and 120 respectively. As can be seen, conductive pathway 116 joins or is formed integrally with conductive pathway 102, conductive pathway 118 joins or is formed integrally with conductive pathway 104, and conductive pathway 120 joins or is formed integrally with conductive pathway 120.

Figure 7:
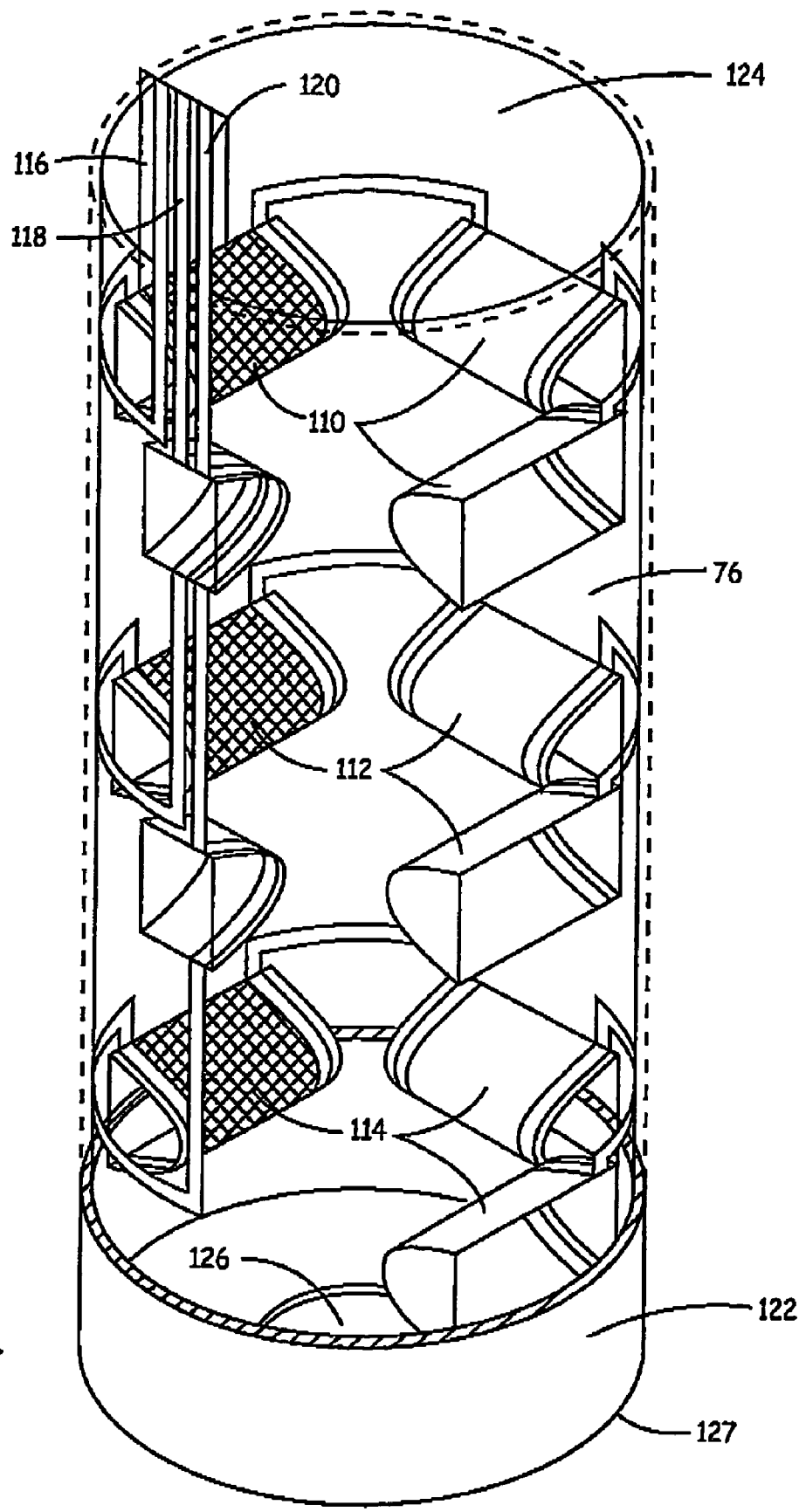
FIG. 7 is an isometric view of a portion of the flexible substrate shown in FIG. 5 positioned within a cylindrical housing in accordance with a first embodiment of the present invention.
Figure 9:
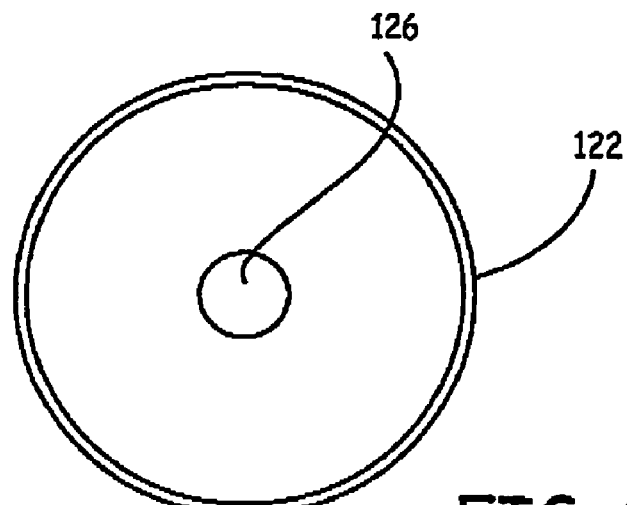
FIG. 9 is an end view of the housing shown in FIG. 7.
Figure 8:
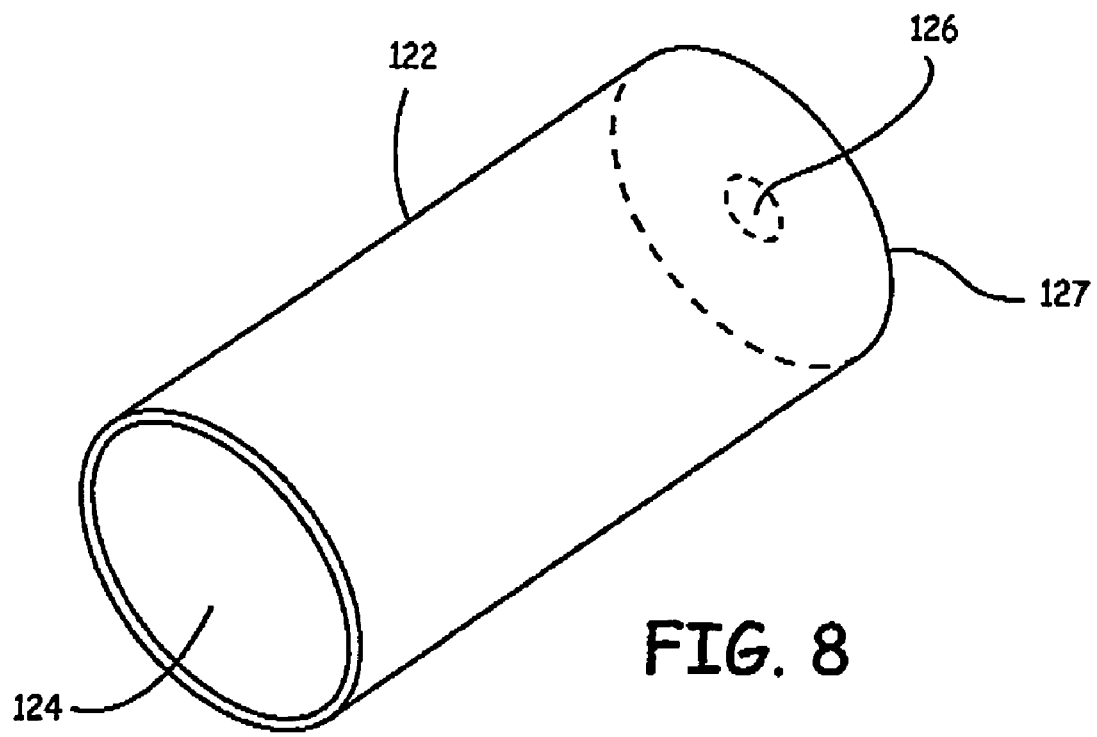
FIG. 8 is an isometric view of the housing shown in FIG. 7.
Figure 10:
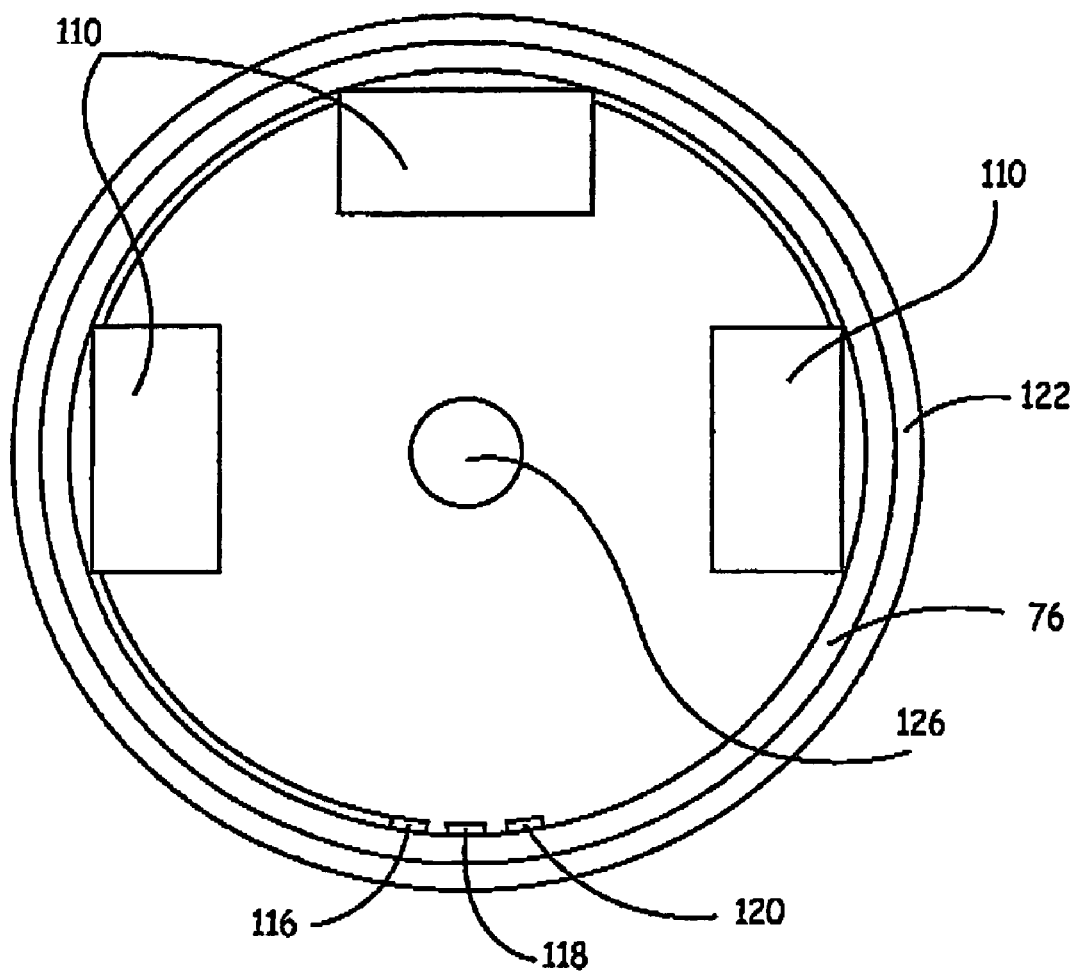
FIG. 10 is an end view of the assembly shown in FIG. 7.

FIG. 7 and FIG. 10 are isometric cutaway and end views respectively of internal contact portion 72 of flexible circuit 70 after being folded or rolled and inserted into a housing 122; e.g. a generally cylindrical housing made of, for example a hard plastic and having an open first end 124 for receiving the folded or rolled flexible circuit. A second or opposite end 127 of housing 122 includes an aperture 126 therein to allow passage of pin contact 58 (FIG. 2). Housing 122 is more clearly shown in FIG. 8 and FIG. 9, which are isometric and end views respectively of housing 122. Internal contact portion 76 of flexible circuit 70 is rolled and inserted into cylindrical housing 122. Three-sets of conductive protrusions 110, 112, and 114 (e.g. folds or dimples) project or extend radially inward as is shown. FIG. 7 depicts conductive protrusions 110, 112, and 114 project or extend radially inward to form convex folds. Only one of each of the contact protrusions 110, 112, and 114 is shaded for clarity. While three rows of three contact areas (i.e. 110, 112, and 114) are shown, it should be appreciated that the number of rows and the number of contacts in each row may be varied to suit a particular application. This also applies to the longitudinal and transverse spacing between contact areas.

Conductive pathway 116 extends into housing 122 and generally circumferentially around the rolled flexible substrate 72 so as to make electrical contact with all of contact areas 110. In a similar fashion, conductive pathway 118 extends longitudinally further into and then circumferentially around housing 122 to make electrical contact with conductive areas 112, and conductive pathway 120 extends longitudinally still further into and then circumferentially around housing 122 to make electrical contact with conductive areas 114. Conductive pathways 116, 118, and 120 exit housing 122 and are coupled to contact pads 96, 98, and 100 via conductive pathways 102, 104, and 106 respectively as is shown in FIG. 5.

Thus, connector 50 of lead body 32 shown in FIG. 2 may be inserted or press-fit into housing 122 until pin contact 58 (FIG. 2) exits aperture 126 and ring contacts 52, 54, and 56 (FIG. 2) come into and are maintained in electrical contact with conductive areas 114, 112, and 110 respectively. Once so positioned, external medical device 43 (FIG. 1A) may be electrically coupled to connector 50 of cardiac lead 32 by connecting alligator clips 38 (FIG. 1A) to one or more of contact pads 96, 98, and 100 (FIG. 5).

Thus, there has been provided a number of embodiments of a medical lead adaptor assembly, each of which facilitates electrical coupling between the proximal lead connector end assembly of a cardiac or similar lead with an external medical device. The lead adaptor is capable of being coupled to the external electrical conductors by means of conductive probes, clips, and the like. The inventive medical lead adaptor assembly may be configured to accept lead connectors that may or may not utilize a stylet wire or guide wire. Furthermore, the inventive lead adaptor may be utilized in conjunction with leads and wires that have compatible lead connector or element dimensions; i.e. compatible assemblies in accordance with the present invention may be provided with different dimensions so as to accommodate a variety of cardiac or other types of leads.

While specific embodiments have been presented in the foregoing detailed description of the invention, it should be clear that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road-map for implementing an exemplary embodiment of the invention. It should be understood that various changes may be made in the function and arrangement of elements described in an exemplary embodiments without departing from the scope of the invention as set forth in the appended claims. For example, a second portion carrying contact pads of the flexible circuit, as described herein, which is adapted to reside outside a housing of the adaptor according to the present invention, may extend from the housing through a longitudinally extending slot of the housing rather than from a distal or first end as illustrated; furthermore, the second portion of the flexible circuit may wrap around an outer surface of the housing.

The invention claimed is:

1. An adaptor facilitating an electrical connection between an elongated connector of an implantable medical lead and an external medical device, the elongated connector including at least one annular ring contact, the adaptor comprising:
   a flexible substrate including a first portion and a second portion;
   at least one contact portion fowled on the first portion of the flexible substrate;
   at least one contact pad formed on the second portion of the flexible substrate; and
   at least one conductive pathway formed on the flexible substrate and coupling the at least one contact portion to the at least one contact pad,
   wherein the first portion of the flexible substrate is adapted to be rolled into a substantially tubular body having an elongated cavity therethrough suitable for receiving the elongated connector, wherein the at least one contact portion comprises at least one convex fold protruding radially into the elongated cavity when the first portion is rolled into the substantially tubular body, and further wherein the at least one convex fold of the at least one contact portion is configured to contact the at least one annular ring contact when the first portion is rolled into the substantially tubular body and the elongated connector is received within the elongated cavity.

2. The adaptor of claim 1 wherein the flexible substrate further includes a third portion coupled to the second portion for detachably engaging the implantable medical lead.

3. The adaptor of claim 2, wherein the third portion includes an aperture therethrough for detachably engaging the implantable medical lead.

4. The adaptor of claim 3, wherein the third portion further includes a slit extending from said aperture to an edge of the third portion.

5. The adaptor of claim 1, wherein the at least one contact portion comprises a plurality of conductive protrusions arranged in a row in the elongated cavity of the substantially tubular body and protruding radially into the elongated cavity when the first portion is rolled into the substantially tubular body, and further wherein the plurality of conductive protrusions of each of the at least one contact portion is configured to circumferentially engage one annular ring contact of the at least one annular ring contact when the first portion is rolled into the substantially tubular body and the elongated connector is received within the elongated cavity of the substantially tubular body.

6. The adaptor of claim 1 further comprising a housing including a substantially cylindrical cavity configured to receive the first portion of the flexible substrate therein to maintain the first portion rolled into the substantially tubular body, wherein the first portion is rolled in the substantially tubular body and positioned within the substantially cylindrical cavity of the housing.

7. The adaptor of claim 6, wherein the housing has a horseshoe-shaped cross-section including first and second leg portions, the first and second leg portions curled inward to form first and second capture portions, respectively, for securing the first portion of the flexible substrate within the substantially cylindrical cavity of the housing.

8. The adaptor of claim 6 wherein the substantially cylindrical cavity has an inner diameter substantially equivalent to the outer diameter of said substantially tubular body.

9. The adaptor of claim 8 wherein the substantially cylindrical cavity has a length substantially equivalent to the length of said substantially tubular body.

10. An adaptor facilitating an electrical connection between a connector of an implantable medical lead and an external medical device, the elongated connector including at least one annular ring contact, the adaptor comprising:
    a flexible substrate including a first portion and a second portion, wherein the first portion of the flexible substrate is adapted to be rolled into a substantially tubular body defining an elongated connector cavity therein configured to receive the elongated connector;
    a plurality of raised conductive protrusions on the first portion of the flexible substrate, wherein each of the plurality of raised conductive protrusions comprises at least one convex fold projecting radially into the elongated connector cavity when the first portion is rolled into the substantially tubular body, and further wherein each of the plurality of raised conductive protrusions contacts one of the at least one ring contact of the elongated connector when the first portion is rolled into the substantially tubular body and the elongated connector is received within the elongated connector cavity;
    a plurality of contact pads formed on the second portion of the flexible substrate;
    a plurality of conductive pathways formed on the flexible substrate, wherein each of the plurality of conductive pathways couples one raised conductive protrusion of the plurality of raised conductive protrusions to one contact pad of the plurality of contact pads such that each raised conductive protrusion of the plurality of raised conductive protrusions is coupled to a different contact pad of the plurality of contact pads; and
    a housing including a substantially cylindrical cavity configured to retain the first portion of the flexible substrate therein and maintain the first portion of the flexible substrate rolled into the substantially tubular body when the first portion is positioned within the substantially cylindrical cavity,
    wherein the second portion of the flexible substrate is adapted to reside outside the housing such that the plurality of contact pads are accessible for coupling to a plurality of contact elements of the external medical device.

11. The adaptor of claim 10, wherein the flexible substrate further includes a third portion adapted to reside outside the housing for detachably engaging the implantable medical lead.

12. The adaptor of claim 10, wherein the housing further includes a proximal end, a distal end, an outer surface and a longitudinal slot extending from the proximal end to the distal end and passing from the outer surface to the substantially cylindrical cavity.

13. The adaptor of claim 12, wherein the housing has a horseshoe-shaped cross-section and the outer surface bends in toward the substantially cylindrical cavity along the length of the slot forming capture portions for securing the first portion of the flexible substrate within the substantially cylindrical cavity of the housing.

14. The adaptor of claim 10 wherein the plurality of conductive protrusions comprises a plurality of annular rows of conductive protrusions spaced apart along the longitudinal axis of the substantially tubular body.

15. The adaptor of claim 14 wherein each annular row of the plurality of annular rows of conductive protrusions are spaced apart from one another such that each annular row of the plurality of annular rows contacts a different ring contact of the at least one annular ring contact of the elongated connector when the elongated connector is received within the elongated cavity of the substantially tubular body.

16. A method for connecting an elongated connector of an implantable medical lead to an external medical device utilizing an adaptor, the adaptor comprising a housing defining a substantially cylindrically cavity and a flexible circuit including a first portion and a second portion, the first portion having a conductive protrusion thereon and the second portion having a conductive pad thereon electrically coupled to the conductive protrusion, the method comprising:
   rolling the first portion into a substantially tubular body, the substantially tubular body having a cavity therein into which the conductive protrusion projects forming a convex fold;
   inserting the substantially tubular body into the substantially cylindrical cavity of the housing such that the housing maintains the first portion rolled into the substantially tubular body;
   inserting the elongated connector into the cavity of the substantially tubular body until at least one contact ring of the connector makes electrical contact with the conductive protrusion of the first portion of the flexible circuit; and
   coupling a contact element of the external medical device to the contact pad of the second portion of the flexible circuit.

17. The method of claim 16, further comprising removably attaching a third portion of the flexible circuit to the implantable medical lead.

18. An adaptor configured to electrically couple an external medical device to an implantable medical device having a connector including a plurality of annular ring contacts thereon, the adapter comprising:
   a first flexible substrate portion having a first surface, wherein said first flexible substrate portion is configured to be rolled into a substantially tubular body such that said first surface defines a cylindrical cavity dimensioned to receive the connector therein;
   a second substrate portion coupled to said first flexible substrate portion;
   a plurality of conductive pads disposed on said second substrate portion;
   a plurality of contact portions disposed on said first surface of the first flexible substrate portion; and
   a plurality of conductive pathways electrically coupling said plurality of conductive portions and said plurality of conductive pads,
   wherein the plurality of contact portions of said first flexible substrate portion are deformed radially inward into the cylindrical cavity to form convex folds when said first flexible substrate portion is rolled into said substantially tubular body, and further wherein said contact portions circumferentially engage the plurality of annular ring contacts of the connector when the first flexible substrate portion is rolled into the substantially tubular body and the connector is inserted into the cylindrical cavity of the substantially tubular body.

19. An adaptor configured to electrically couple an external medical device to an implantable medical device having a connector including a plurality of annular ring contacts thereon, the adapter comprising:
   a first flexible substrate portion having a first surface, wherein said first flexible substrate portion is configured to be rolled into a substantially tubular body such that said first surface defines a cylindrical cavity through said substantially tubular body dimensioned to receive the connector therein;
   a second substrate portion coupled to said first flexible substrate portion;
   a plurality of conductive pads disposed on said second substrate portion;
   a plurality of contact portions disposed on said first surface of the first flexible substrate portion;
   a plurality of conductive pathways electrically coupling said plurality of conductive portions and said plurality of conductive pads; and
   a housing defining a cavity for receiving the first flexible substrate portion and for maintaining the first flexible substrate portion rolled into said substantially tubular body, wherein the first flexible substrate portion is positioned within the cavity of the housing such that the first flexible substrate portion is rolled into and maintained as the substantially tubular body and the plurality of contact portions of the first flexible substrate portion are deformed radially inward to form convex folds protruding into the cylindrical cavity of the substantially tubular body.

20. An adaptor configured to electrically couple an external medical device to an implantable medical device having a connector including a plurality of annular ring contacts thereon, the adapter comprising:
   a first flexible substrate portion having a first surface, wherein said first flexible substrate portion is rolled into and maintained as a substantially tubular body such that said first surface defines a cylindrical cavity dimensioned to receive the connector therein;
   a second substrate portion coupled to said first flexible substrate portion;
   a plurality of conductive pads disposed on said second substrate portion;
   a plurality of contact portions disposed on said first surface of the first flexible substrate portion, wherein the plurality of conductive portions are deformed inwardly to form convex folds protruding into the cylindrical cavity; and
   a plurality of conductive pathways electrically coupling said plurality of conductive portions and said plurality of conductive pads.

21. A female adaptor configured to electrically couple an external medical device to an implantable medical device having a connector including a plurality of annular ring contacts thereon, the adapter comprising:
   a flexible substrate with contact portions, wherein the flexible substrate is rolled into and maintained as a substantially tubular body such that the contact portions deform inward to form convex folds protruding into a cavity defined by the substantially tubular body, and further wherein the convex folds are configured to contact the annular ring contacts of the connector of the implantable medical device when the connector is positioned within the cavity of the substantially tubular body.

22. An adaptor for receiving a connector, wherein the adaptor comprises:
a housing defining a circuit-receiving cavity; and
a substrate comprising:
a first portion comprising:
a connection surface, and
at least one electrical contact protrusion located on the connection surface,
wherein the first portion is flexible, and
a second portion, wherein the second portion comprises at least one electrical contact portion, wherein the at least one electrical contact protrusion of the first portion is electrically coupled to the at least one electrical contact portion of the second portion,
wherein the first portion of the substrate is positioned within the circuit-receiving cavity of the housing such that the first portion is rolled or folded to at least partially conform to the circuit-receiving cavity, thereby defining a connector-receiving cavity with the connection surface, and further wherein the at least one electrical contact protrusion extends into the connector-receiving cavity to contact the connector when the connector is positioned within the connector-receiving cavity.

23. The adaptor of claim 22, wherein the second portion is located outside of the circuit-receiving cavity of the housing.

24. The adaptor of claim 22, wherein the at least one electrical contact protrusion electrically engages the connector when the connector is located within the connector-receiving cavity.

25. The adaptor of claim 22, wherein the at least one electrical contact protrusion mechanically engages the connector when the connector is located within the connector-receiving cavity to assist in retaining the connector within the connector-receiving cavity.

26. The adaptor of claim 22, wherein the at least one contact protrusion comprises at least one annular row of two or more contact protrusions.

27. The adaptor of claim 22, wherein the at least one contact protrusion comprises at least two annular rows of two or more contact protrusions, and further wherein each annular row of the at least two annular rows of two or more contact protrusions is spaced apart along a longitudinal axis of the connector-receiving cavity.

28. The adaptor of claim 22, wherein the at least one contact protrusion comprises a convex fold of conductive material protruding from the first portion of the flexible circuit into the connector-receiving cavity.

* * * * *